(12) United States Patent
Vortman et al.

(10) Patent No.: US 8,608,672 B2
(45) Date of Patent: Dec. 17, 2013

(54) HIERARCHICAL SWITCHING IN ULTRA-HIGH DENSITY ULTRASOUND ARRAY

(75) Inventors: Kobi Vortman, Haifa (IL); Yoav Medan, Haifa (IL); Avner Ezion, Haifa (IL)

(73) Assignee: Insightec Ltd., Tirat Carmel (IL)

( * ) Notice: Subject to any disclaimer, the term of this patent is extended or adjusted under 35 U.S.C. 154(b) by 1047 days.

(21) Appl. No.: 11/562,749

(22) Filed: Nov. 22, 2006

(65) Prior Publication Data

US 2007/0167781 A1    Jul. 19, 2007

Related U.S. Application Data

(60) Provisional application No. 60/739,862, filed on Nov. 23, 2005.

(51) Int. Cl.
*A61H 1/00* (2006.01)

(52) U.S. Cl.
USPC .......................................................... 601/2

(58) Field of Classification Search
USPC .......................................................... 601/2
See application file for complete search history.

(56) References Cited

U.S. PATENT DOCUMENTS

| | | |
|---|---|---|
| 2,795,709 A | 6/1957 | Camp |
| 3,142,035 A | 7/1964 | Harris |
| 3,942,150 A | 3/1976 | Booth et al. |
| 3,974,475 A | 8/1976 | Burckhardt et al. |
| 3,992,693 A | 11/1976 | Martin et al. |
| 4,000,493 A * | 12/1976 | Spaulding et al. ............ 347/255 |
| 4,074,564 A | 2/1978 | Anderson |
| 4,206,653 A | 6/1980 | Lemay |
| 4,221,132 A | 9/1980 | Poole |
| 4,307,613 A | 12/1981 | Fox |
| 4,339,952 A | 7/1982 | Foster |
| 4,454,597 A | 6/1984 | Sullivan |
| 4,478,083 A | 10/1984 | Hassler et al. |

(Continued)

FOREIGN PATENT DOCUMENTS

| | | |
|---|---|---|
| DE | 4345308 | 2/2001 |
| EP | 320303 | 6/1989 |

(Continued)

OTHER PUBLICATIONS

Exablate 2000 Specification.*

(Continued)

*Primary Examiner* — Tse Chen
*Assistant Examiner* — Hien Nguyen
(74) *Attorney, Agent, or Firm* — Bingham McCutchen LLP (57) ABSTRACT

A focused ultrasound system comprises a transducer having a multiplicity of transducer elements, drive circuitry that generates and outputs a plurality of drive signals, each offset by a respective phase difference, and a controller for selectively coupling the drive signals to respective transducer elements, the controller including a plurality of first tier switching modules and second tier switching modules. Each first tier module receives as an input the plurality of drive signals and outputs one of the drive signals in response to a drive signal selection signal. Each second tier module is coupled to a respective grouping of transducer elements and selectively couples a respective selected drive signal output from a first tier switching module to one or more of the transducer elements in response to a transducer element selection signal.

12 Claims, 6 Drawing Sheets

(56) References Cited

U.S. PATENT DOCUMENTS

| | | | |
|---|---|---|---|
| 4,505,156 A | 3/1985 | Questo | |
| 4,526,168 A | 7/1985 | Hassler et al. | |
| 4,537,074 A | 8/1985 | Dietz | |
| 4,549,533 A | 10/1985 | Cain et al. | |
| 4,554,925 A | 11/1985 | Young | |
| 4,636,964 A * | 1/1987 | Jacobs et al. | 700/298 |
| 4,662,222 A | 5/1987 | Johnson | |
| 4,817,614 A | 4/1989 | Hassler et al. | |
| 4,858,597 A | 8/1989 | Kurtze et al. | |
| 4,865,042 A | 9/1989 | Umemura et al. | |
| 4,888,746 A | 12/1989 | Wurster et al. | |
| 4,889,122 A | 12/1989 | Watmough et al. | |
| 4,893,284 A | 1/1990 | Magrane | |
| 4,893,624 A | 1/1990 | Lele | |
| 4,937,767 A | 6/1990 | Reuschel et al. | |
| 5,197,475 A | 3/1993 | Antich et al. | |
| 5,209,221 A | 5/1993 | Riedlinger | |
| 5,211,160 A | 5/1993 | Talish et al. | |
| 5,247,935 A | 9/1993 | Cline et al. | |
| 5,271,400 A | 12/1993 | Dumoulin et al. | |
| 5,275,165 A | 1/1994 | Ettinger et al. | |
| 5,291,890 A | 3/1994 | Cline et al. | |
| 5,307,812 A | 5/1994 | Hardy et al. | |
| 5,307,816 A | 5/1994 | Hashimoto et al. | |
| 5,318,025 A | 6/1994 | Dumoulin et al. | |
| 5,323,779 A | 6/1994 | Hardy et al. | |
| 5,327,884 A | 7/1994 | Hardy et al. | |
| 5,329,930 A | 7/1994 | Thomas, III et al. | |
| 5,368,031 A | 11/1994 | Cline et al. | |
| 5,368,032 A | 11/1994 | Cline et al. | |
| 5,379,642 A | 1/1995 | Reckwerdt et al. | |
| 5,391,140 A | 2/1995 | Schaetzle et al. | |
| 5,413,550 A | 5/1995 | Castel | |
| 5,435,312 A | 7/1995 | Spivey et al. | |
| 5,443,068 A | 8/1995 | Cline et al. | |
| 5,474,071 A | 12/1995 | Chapelon et al. | |
| 5,485,839 A | 1/1996 | Aida et al. | |
| 5,490,840 A | 2/1996 | Uzgiris et al. | |
| 5,507,790 A | 4/1996 | Weiss | |
| 5,520,188 A | 5/1996 | Hennige et al. | |
| 5,520,612 A | 5/1996 | Winder et al. | |
| 5,526,814 A | 6/1996 | Cline et al. | |
| 5,549,638 A | 8/1996 | Burdette | |
| 5,553,618 A | 9/1996 | Suzuki et al. | |
| 5,573,497 A | 11/1996 | Chapelon | |
| 5,582,578 A | 12/1996 | Zhong et al. | |
| 5,590,653 A | 1/1997 | Aida et al. | |
| 5,590,657 A | 1/1997 | Cain et al. | |
| 5,601,526 A | 2/1997 | Chapelon et al. | |
| 5,605,154 A | 2/1997 | Ries et al. | |
| 5,606,971 A | 3/1997 | Sarvazyan | |
| 5,617,371 A | 4/1997 | Williams | |
| 5,617,857 A | 4/1997 | Chader et al. | |
| 5,643,179 A | 7/1997 | Fujimoto | |
| 5,662,170 A | 9/1997 | Donovan et al. | |
| 5,665,054 A | 9/1997 | Dory | |
| 5,666,954 A | 9/1997 | Chapelon et al. | |
| 5,676,673 A | 10/1997 | Ferre et al. | |
| 5,687,729 A | 11/1997 | Schaetzle | |
| 5,694,936 A | 12/1997 | Fujimoto et al. | |
| 5,711,300 A | 1/1998 | Schneider et al. | |
| 5,722,411 A | 3/1998 | Suzuki et al. | |
| 5,728,062 A | 3/1998 | Brisken | |
| 5,739,625 A | 4/1998 | Falcus | |
| 5,743,863 A | 4/1998 | Chapelon | |
| 5,752,515 A | 5/1998 | Jolesz et al. | |
| 5,759,162 A | 6/1998 | Oppelt et al. | |
| 5,762,616 A | 6/1998 | Talish | |
| 5,769,790 A | 6/1998 | Watkins et al. | |
| 5,810,008 A | 9/1998 | Dekel et al. | |
| 5,810,731 A | 9/1998 | Sarvazyan et al. | |
| 5,873,845 A | 2/1999 | Cline et al. | |
| 5,897,495 A | 4/1999 | Aida et al. | |
| 5,904,659 A | 5/1999 | Duarte et al. | |
| 5,938,600 A | 8/1999 | Van Vaals et al. | |
| 5,938,608 A | 8/1999 | Bieger et al. | |
| 5,947,900 A | 9/1999 | Derbyshire et al. | |
| 5,984,881 A | 11/1999 | Ishibashi et al. | |
| 6,004,269 A | 12/1999 | Crowley et al. | |
| 6,023,636 A | 2/2000 | Wendt et al. | |
| 6,042,556 A | 3/2000 | Beach et al. | |
| 6,071,239 A | 6/2000 | Cribbs et al. | |
| 6,113,559 A | 9/2000 | Klopotek | |
| 6,128,522 A | 10/2000 | Acker et al. | |
| 6,128,958 A | 10/2000 | Cain | |
| 6,135,960 A | 10/2000 | Holmberg | |
| 6,193,659 B1 | 2/2001 | Ramamurthy et al. | |
| 6,217,530 B1 | 4/2001 | Martin et al. | |
| 6,242,915 B1 | 6/2001 | Hurd | |
| 6,246,896 B1 | 6/2001 | Dumoulin et al. | |
| 6,263,230 B1 | 7/2001 | Haynor et al. | |
| 6,267,734 B1 | 7/2001 | Ishibashi et al. | |
| 6,289,233 B1 | 9/2001 | Dumoulin et al. | |
| 6,309,355 B1 | 10/2001 | Cain et al. | |
| 6,317,619 B1 | 11/2001 | Boernert et al. | |
| 6,322,527 B1 | 11/2001 | Talish | |
| 6,334,846 B1 | 1/2002 | Ishibashi et al. | |
| 6,374,132 B1 | 4/2002 | Acker et al. | |
| 6,392,330 B1 | 5/2002 | Zloter et al. | |
| 6,397,094 B1 | 5/2002 | Ludeke et al. | |
| 6,413,216 B1 | 7/2002 | Cain et al. | |
| 6,419,648 B1 | 7/2002 | Vitek et al. | |
| 6,424,597 B1 | 7/2002 | Bolomey et al. | |
| 6,425,867 B1 | 7/2002 | Vaezy et al. | |
| 6,428,532 B1 | 8/2002 | Doukas et al. | |
| 6,433,464 B2 | 8/2002 | Jones | |
| 6,461,314 B1 | 10/2002 | Pant et al. | |
| 6,475,150 B2 | 11/2002 | Haddad | |
| 6,478,739 B1 | 11/2002 | Hong | |
| 6,506,154 B1 | 1/2003 | Ezion et al. | |
| 6,506,171 B1 | 1/2003 | Vitek et al. | |
| 6,511,428 B1 | 1/2003 | Azuma et al. | |
| 6,522,142 B1 | 2/2003 | Freundlich | |
| 6,523,272 B1 | 2/2003 | Morales | |
| 6,524,251 B2 | 2/2003 | Rabiner et al. | |
| 6,559,644 B2 | 5/2003 | Froundlich et al. | |
| 6,566,878 B1 | 5/2003 | Komura et al. | |
| 6,582,381 B1 | 6/2003 | Yehezkeli et al. | |
| 6,599,256 B1 | 7/2003 | Acker et al. | |
| 6,612,988 B2 | 9/2003 | Maor et al. | |
| 6,613,004 B1 | 9/2003 | Vitek et al. | |
| 6,613,005 B1 | 9/2003 | Friedman et al. | |
| 6,618,608 B1 | 9/2003 | Watkins et al. | |
| 6,618,620 B1 | 9/2003 | Freundlich et al. | |
| 6,626,854 B2 | 9/2003 | Friedman et al. | |
| 6,626,855 B1 | 9/2003 | Weng et al. | |
| 6,629,929 B1 | 10/2003 | Jago et al. | |
| 6,645,162 B2 | 11/2003 | Friedman et al. | |
| 6,652,461 B1 | 11/2003 | Levkovitz | |
| 6,666,833 B1 | 12/2003 | Friedman et al. | |
| 6,676,601 B1 | 1/2004 | Lacoste et al. | |
| 6,676,602 B1 | 1/2004 | Barnes et al. | |
| 6,679,855 B2 | 1/2004 | Horn et al. | |
| 6,705,994 B2 | 3/2004 | Vortman et al. | |
| 6,719,694 B2 | 4/2004 | Weng et al. | |
| 6,733,450 B1 | 5/2004 | Alexandrov et al. | |
| 6,735,461 B2 | 5/2004 | Vitek et al. | |
| 6,761,691 B2 | 7/2004 | Tsuzuki | |
| 6,770,031 B2 | 8/2004 | Hynynen et al. | |
| 6,770,039 B2 | 8/2004 | Zhong et al. | |
| 6,788,619 B2 | 9/2004 | Calvert | |
| 6,790,180 B2 | 9/2004 | Vitek | |
| 6,824,516 B2 | 11/2004 | Batten et al. | |
| 6,951,540 B2 | 10/2005 | Ebbini et al. | |
| 6,961,606 B2 | 11/2005 | DeSilets et al. | |
| 7,001,379 B2 | 2/2006 | Behl et al. | |
| 7,077,820 B1 | 7/2006 | Kadziauskas et al. | |
| 7,094,205 B2 | 8/2006 | Marmarelis | |
| 7,128,711 B2 | 10/2006 | Medan et al. | |
| 7,155,271 B2 | 12/2006 | Halperin et al. | |
| 7,175,596 B2 | 2/2007 | Vitek et al. | |
| 7,175,599 B2 | 2/2007 | Hynynen et al. | |
| 7,264,592 B2 | 9/2007 | Shehada | |
| 7,264,597 B2 | 9/2007 | Cathignol | |

(56) References Cited

U.S. PATENT DOCUMENTS

| | | |
|---|---|---|
| 7,267,650 B2 | 9/2007 | Chow et al. |
| 7,344,509 B2 | 3/2008 | Hynynen et al. |
| 7,377,900 B2 | 5/2008 | Vitek et al. |
| 7,429,248 B1 | 9/2008 | Winder et al. |
| 7,452,357 B2 | 11/2008 | Vlegele et al. |
| 7,505,805 B2 | 3/2009 | Kuroda |
| 7,505,808 B2 | 3/2009 | Anderson et al. |
| 7,507,213 B2 | 3/2009 | Schultheiss et al. |
| 7,510,536 B2 | 3/2009 | Foley et al. |
| 7,511,501 B2 | 3/2009 | Wexler |
| 7,535,794 B2 | 5/2009 | Prus et al. |
| 7,553,284 B2 | 6/2009 | Vaitekunas |
| 7,603,162 B2 | 10/2009 | Danz et al. |
| 7,611,462 B2 | 11/2009 | Vortman et al. |
| 7,652,410 B2 | 1/2010 | Prus |
| 7,699,780 B2 | 4/2010 | Vitek et al. |
| 2001/0031922 A1* | 10/2001 | Weng et al. ............... 600/439 |
| 2002/0016557 A1 | 2/2002 | Duarte et al. |
| 2002/0035779 A1 | 3/2002 | Krieg et al. |
| 2002/0082589 A1 | 6/2002 | Friedman et al. |
| 2002/0095087 A1 | 7/2002 | Mourad et al. |
| 2002/0111552 A1 | 8/2002 | Maor et al. |
| 2002/0161300 A1 | 10/2002 | Hoff et al. |
| 2002/0188229 A1 | 12/2002 | Ryaby |
| 2003/0004439 A1 | 1/2003 | Pant et al. |
| 2003/0060820 A1 | 3/2003 | Maguire et al. |
| 2003/0187371 A1 | 10/2003 | Vortman et al. |
| 2004/0030251 A1 | 2/2004 | Ebbini et al. |
| 2004/0059265 A1 | 3/2004 | Candy et al. |
| 2004/0068186 A1 | 4/2004 | Ishida et al. |
| 2004/0122316 A1 | 6/2004 | Satoh |
| 2004/0122323 A1 | 6/2004 | Vortman et al. |
| 2004/0143187 A1 | 7/2004 | Biagi et al. |
| 2004/0210134 A1 | 10/2004 | Hynynen et al. |
| 2004/0210135 A1 | 10/2004 | Hynynen et al. |
| 2004/0236253 A1 | 11/2004 | Vortman et al. |
| 2004/0267126 A1* | 12/2004 | Takeuchi ............... 600/447 |
| 2005/0033201 A1 | 2/2005 | Takahashi et al. |
| 2005/0096542 A1 | 5/2005 | Weng et al. |
| 2005/0131301 A1 | 6/2005 | Peszynski et al. |
| 2005/0203444 A1 | 9/2005 | Schonenberger et al. |
| 2005/0251046 A1 | 11/2005 | Yamamoto et al. |
| 2006/0052661 A1 | 3/2006 | Gannot et al. |
| 2006/0052701 A1 | 3/2006 | Carter et al. |
| 2006/0052706 A1 | 3/2006 | Hynynen et al. |
| 2006/0058678 A1 | 3/2006 | Vitek et al. |
| 2006/0106300 A1 | 5/2006 | Seppenwoolde et al. |
| 2006/0173385 A1 | 8/2006 | Lidgren et al. |
| 2006/0184034 A1 | 8/2006 | Haim et al. |
| 2006/0184069 A1 | 8/2006 | Vaitekunas |
| 2006/0206105 A1 | 9/2006 | Chopra et al. |
| 2006/0229594 A1 | 10/2006 | Francischelli et al. |
| 2007/0016039 A1 | 1/2007 | Vortman et al. |
| 2007/0055140 A1 | 3/2007 | Kuroda |
| 2007/0066897 A1 | 3/2007 | Sekins et al. |
| 2007/0073135 A1 | 3/2007 | Lee et al. |
| 2007/0098232 A1 | 5/2007 | Matula et al. |
| 2007/0167781 A1 | 7/2007 | Vortman et al. |
| 2007/0197918 A1 | 8/2007 | Vitek et al. |
| 2007/0219470 A1 | 9/2007 | Talish et al. |
| 2007/0239062 A1 | 10/2007 | Chopra et al. |
| 2007/0276237 A1 | 11/2007 | Li |
| 2008/0027342 A1* | 1/2008 | Rouw et al. ............... 600/513 |
| 2008/0031090 A1 | 2/2008 | Prus et al. |
| 2008/0033278 A1 | 2/2008 | Assif |
| 2008/0082026 A1 | 4/2008 | Schmidt et al. |
| 2008/0108900 A1 | 5/2008 | Lee et al. |
| 2008/0125660 A1 | 5/2008 | Yao et al. |
| 2008/0183077 A1 | 7/2008 | Moreau-Gobard et al. |
| 2008/0228081 A1 | 9/2008 | Becker et al. |
| 2008/0312562 A1 | 12/2008 | Routh et al. |
| 2009/0088623 A1 | 4/2009 | Vortman et al. |
| 2009/0118619 A1 | 5/2009 | Oshiki |
| 2010/0030076 A1 | 2/2010 | Vortman et al. |
| 2010/0056962 A1 | 3/2010 | Vortman et al. |
| 2010/0125193 A1 | 5/2010 | Zadicario |
| 2010/0179425 A1 | 7/2010 | Zadicario |
| 2010/0268088 A1 | 10/2010 | Prus et al. |
| 2010/0318002 A1 | 12/2010 | Prus et al. |
| 2011/0066032 A1 | 3/2011 | Vitek et al. |
| 2011/0094288 A1 | 4/2011 | Medan et al. |

FOREIGN PATENT DOCUMENTS

| | | |
|---|---|---|
| EP | 0558029 | 9/1993 |
| EP | 1132054 | 9/2001 |
| EP | 151073 | 11/2005 |
| EP | 1774920 | 4/2007 |
| EP | 1790384 | 5/2007 |
| EP | 1936404 | 6/2008 |
| FR | 2806611 | 8/2002 |
| JP | 592008 | 4/1993 |
| JP | 7231895 | 9/1995 |
| JP | 7313518 | 12/1995 |
| JP | 11313833 | 11/1999 |
| JP | 2000-166940 | 6/2000 |
| JP | 2001-516075 | 9/2001 |
| JP | 2002-530145 | 9/2002 |
| JP | 2007-184907 | 7/2007 |
| WO | WO-91/00059 | 1/1991 |
| WO | WO-95/14505 | 6/1995 |
| WO | WO-98/52465 | 11/1998 |
| WO | WO-00/31614 | 6/2000 |
| WO | WO-01/58337 | 8/2001 |
| WO | WO-01/66189 | 9/2001 |
| WO | WO-01/80709 | 11/2001 |
| WO | WO-02/43805 | 6/2002 |
| WO | WO-02/44753 | 6/2002 |
| WO | WO-02/058791 | 8/2002 |
| WO | WO-03/013654 | 2/2003 |
| WO | WO-03/097162 | 11/2003 |
| WO | WO-03/098232 | 11/2003 |
| WO | WO-2004/093686 | 11/2004 |
| WO | WO-2005/058029 | 6/2005 |
| WO | WO-2006/018837 | 2/2006 |
| WO | WO-2006/025001 | 3/2006 |
| WO | WO-2006/087649 | 8/2006 |
| WO | WO-2006/119572 | 11/2006 |
| WO | WO-2007/051066 | 5/2007 |
| WO | WO-2007/073551 | 6/2007 |
| WO | WO-2008/039449 | 4/2008 |
| WO | WO-2008/050278 | 5/2008 |
| WO | WO-2008/075203 | 6/2008 |
| WO | WO-2008/119054 | 10/2008 |
| WO | WO-2009/055587 | 4/2009 |
| WO | WO-2009/081339 | 7/2009 |
| WO | WO-2009/094554 | 7/2009 |
| WO | WO-2010/058292 | 5/2010 |
| WO | WO-2010/082135 | 7/2010 |
| WO | WO-2010/119340 | 10/2010 |
| WO | WO-2010/143072 | 12/2010 |
| WO | WO-2011/013001 | 2/2011 |
| WO | WO-2011/024074 | 3/2011 |

OTHER PUBLICATIONS

FDA Approves Exablate 2000 As Non-Invasive Surgery for Fibroids, Oct. 22, 2004.*

McGough et al., "Direct Computation of Ultrasound Phased-Array Driving Signals from a Specified Temperature Distribution for Hyperthermia," IEEE Transactions on Biomedical Engineering, vol. 39, No. 8, pp. 825-835 (Aug. 1992).

McDonnald et al. "Usefulness of MR Imaging-Derived Thermometry and Dosimetry in Determining the Threshold for Tissue Damage INduced by Thermal Surgery in Rabbits," Radiology, vol. 216, No. 2000 pp. 517-523 (2000).

Suprijanto et al. "Displacement Correction Scheme for MR-Guided Interstitial Laser Therapy," Ellis RE, Peters TM (Eds.): MiCCAI, LNCS 2879, pp. 399-407 (2003).

Shmatukha et al. "Correction of Proton Resonance Frequencey Shift Temperature Maps for Magnetic Field Disturbances Caused by Breathing," Physics in Medicine and Biology, vol. 51, No. 18 pp. 4689-4705 (2006).

(56) References Cited

OTHER PUBLICATIONS

De Senneville et al., "An Optimised Multi-Baseline Approach for On-Line MR-Temperature Monitoring on Commodity Graphics Hardware," Biomedical Imaging, pp. 1513-1516 (2008).

Vigen et al., "Triggered, Navigated, Multi-Baseline Method for Proton Resonance Frequency Temperature Mapping with Respiratory Motion," Magnetic Resonance in Medicine, vol. 50, pp. 1003-1010 (2003).

English Translation of Third Office Action for Chinese Patent Application No. 200680043932.8 mailed Mar. 31, 2011 (2 pages).

Botros et al., "A hybrid computational model for ultrasound phased-array heating in presence of strongly scattering obstacles," IEEE Trans. On Biomed. Eng., vol. 44, No. 11, pp. 1039-1050 (Nov. 1997).

Cain et al., "Concentric-ring and Sector-vortex Phased-array Applicators for Ultrasound Hperthermia," IEEE Trans. On Microwave Theory & Techniques, vol. MTT-34, No. 5, pp. 542-551 (May 1986).

Chen et al., "MR Acoustic Radiation Force Imaging: Comparison of Encoding Gradients."

Cline et al., "Focused US system for MR imaging-guide tumor ablation," Radiology, v. 194, No. 3, pp. 731-738 (Mar. 1995).

Cline et al., "MR Temperature mapping of focused ultrasound surgery," Magnetic Resonance in Medicine, vol. 32, No. 6, pp. 628-636 (1994).

Cline et al., "Simultaneous magnetic resonance phase and magnitude temperature maps in muscle," Magnetic Resonance in Medicine, vol. 35, No. 3, pp. 309-315 (Mar. 1996).

Daum et al., "Design and evaluation of a feedback based phased array system for ultrasound surgery," IEEE Trans. Ultrason. Ferroelec. Freq. Control, vol. 45, No. 2, pp. 431-434 (1998).

de Senneville et al., "Real-time adaptive methods for treatment of mobile organs by MRI-controlled high-intensity focussed Ultrasound," Magnetic Resonance in Medicine 57:319-330 (2007).

Fjield et al, "The Combined Concentric-ring and Sector-vortex Phased Array for MRI Guided Ultrasound Surgery," IEEE Trans. On Ultrasonics, Ferroelectrics and Freq. Cont., vol. 44, No. 5, pp. 1157-1167 (Sep. 1997).

Herbert et al., "Energy-based adaptive focusing of waves: application to ultrasonic transcranial therapy," 8th Intl. Symp. On Therapeutic Ultrasound.

Huber et al., "A New Noninvasive Approach in Breast Cancer Therapy Using Magnetic Resonance Imaging-Guided Focussed Ultrasound Surgery," Cancer Research 61, 8441-8447 (Dec. 2001).

Jolesz et al., "Integration of interventional MRI with computer-assisted surgery," J. Magnetic Resonance Imaging. 12:69-77 (2001).

Kohler et al., "Volumetric HIFU Ablation guided by multiplane MRI thermometry," 8th Intl. Symp. On Therapeutic Ultrasound, edited by E.S. Ebbini, U. of Minn. (Sep. 2009).

Kowalski et al., "Optimization of electromagnetic phased-arrays for hyperthermia via magnetic resonance temperature estimation," IEEE Trans. On Biomed. Eng., vol. 49, No. 11, pp. 1229-1241 (Nov. 2002).

Maxwell et al., "Noninvasive thrombolysis using pulsed ultrasound cavitation therapy—Histotripsy," Abstract, U.S. Natl. Lib. Of Med., NIH, Ultrasound Med. Biol. (Oct. 23, 2009).

McDannold et al., "MRI evaluation of thermal ablation of tumors and focused ultrasounds," JMRI vol. 8, No. 1, pp. 91-100 (1998).

McDannold et al., "Magnetic resonance acoustic radiation force imaging," Med. Phys. vol. 35, No. 8, pp. 3748-3758 (Aug. 2008).

Medel et al., "Sonothrombolysis: An emerging modality for the management of stroke," Neurosurgery, vol. 65, No. 5, pp. 979-993.

Mougenot et al., "MR monitoring of the near-field HIFU heating," 8th Intl. Symp. On Therapeutic Ultrasound, edited by E.S. Ebbini, U. of Minn. (Sep. 2009).

Vimeux et al., "Real-time control of focused ultrasound heating based on rapid MR thermometry," Investig. Radiology, vol. 43, No. 3, pp. 190-193.

Vykhodtseva et al., "MRI detection of the thermal effects of focused ultrasound on the brain," Ultrasound in Med. & Biol., vol. 26, No. 5, pp. 871-880 (2000).

"How is Ablatherm treatment performed?" http://www.edap-hifu.com/eng/physicians/hifu/3c_treatment_treat-description.htm, accessed Jan. 3, 2003.

"What is HIFU? HIFU: High Intensity Focused Ultrasound," http://www.edap-hifu.com/eng/physicians/hifu2a_hifu_overview.htm, accessed Jan. 3, 2003.

"What are the physical principles?" http://www.edap-hifu.com/eng/physicians/hifu/2c_hifu_physical.htm, accessed Jan. 3, 2003.

"How does HIFU create a lesion?" http://www.edap-hifu.com/eng/physicians/hifu/2d_hifu_lesion.htm, accessed Jan. 3, 2003.

"Prostate Cancer Phase I Clinical Trials Using High Intensity Focused Ultrasound (HIFU)," Focus Surgery, http://www.focus-surgery.com/PCT%20Treatment%20with%20HIFU.htm, accessed Jan. 3, 2003.

"Abstract". Focus Surgery, http://www.focus-surgery.com/Sanghvi.htm, accessed Jan. 3, 2003.

Exablate 2000 Specification, InSightec, Ltd. (2 pages).

Office Action in Chinese Patent Application No. 200680043932.8, mailed May 28, 2010 (7 pages).

Office Action in Chinese Patent Application No. 200680043932.8, mailed Dec. 7, 2010 (7 pages).

International Search Report and Written Opinion issued Feb. 14, 2008 for International Application No. PCT/IB06/03300 (8 pages).

Office Action in Japanese Patent Application No. 2008-541,839, Jan. 23, 2012, 2 pages (translation).

Fronheiser et al., "3D Acoustic Radiation Force Impulse (ARFI) Imaging Using a 2D Matrix Array: Feasibility Study," Ultrasonics Symposium, pp. 1144-1147 (Oct. 2006).

Wu et al., "MR Imaging of Shear Waves Generated by Focused Ultrasound," Magnetic Resonance in Medicine, vol. 43, pp. 111-115 (2000).

Heikkila et al., "Simulations of Lesion Detection Using a Combined Phased Array LHMI-Technique,"Ultrasonics, IPC Science and Technology Press Ltd., vol. 48, No. 6-7, pp. 568-573 (Nov. 2008).

* cited by examiner

HIERARCHICAL SWITCHING IN ULTRA-HIGH DENSITY ULTRASOUND ARRAY

RELATED APPLICATION DATA

The present application claims the benefit under 35 U.S.C. §119 to U.S. provisional patent application Ser. No. 60/739,862, filed Nov. 23, 2005, which is hereby incorporated by reference.

FIELD OF INVENTION

This application relates generally to systems for delivering high intensity, therapeutic acoustic energy from a multi-element transducer, e.g., a high density, phased-array transducer, to a targeted tissue region in a patient.

BACKGROUND

Figure 1:
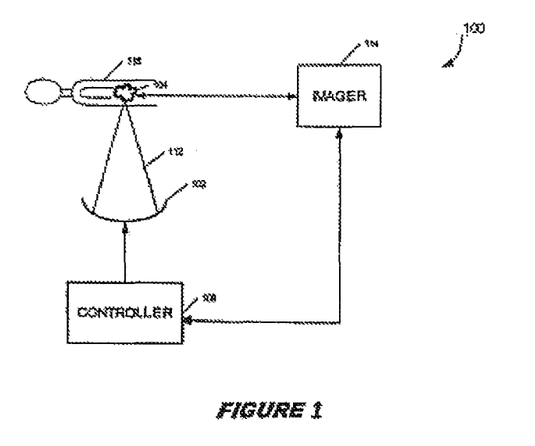
FIGS. 1-2 are simplified schematic representations of an exemplary image-guided focused ultrasound system.

It is well-known to use high intensity, focused acoustic wave energy, such as ultrasonic waves (i.e., acoustic waves having) a frequency greater than about 20 kilohertz) to generate thermal ablation energy for treating internal body tissue, such as tumors. It is also well-known to employ an imaging system, such as a MRI system, in order to guide the delivery of such high intensity ultrasound energy to the targeted tissue area, and to provide real-time feedback of the actual delivered thermal energy. One Such image-guided, focused ultrasound system is the Exablate® 2000 system manufactured and distributed by InSigthtec Ltd, located in Haifa, Israel (www.InSightec.com). By way of illustration, FIG. 1 is a simplified schematic representation of an image-guided, focused ultrasound system 100 used to generate and deliver a focused acoustic energy beam 112 to a targeted tissue mass 104 in a patient 110. The system 100 employs an ultrasound transducer 102 that is geometrically shaped and physically positioned relative to the patient 110 in order to focus the ultrasonic energy beam 112 at a three-dimensional focal zone located within the targeted tissue mass 104. The transducer 102 may be substantially rigid, semi-rigid, or substantially flexible, and can be made from a variety of materials, such as plastics, polymers, metals, and alloys. The transducer 102 can be manufactured as a single unit, or alternatively, be assembled from a plurality of components. While the illustrated transducer 102 has a "spherical cap" shape, a variety of other geometric transducer shapes and configurations may be employed to deliver a focused acoustic beam, including linear (planar) configurations. The ultrasound system 100 may further include a coupling membrane (not shown), such as an inflatable body or a balloon filled with degassed water, for providing or improving the acoustic coupling between the transducer 102 and the skin surface of the patient 110.

The transducer 102 may be formed of relatively large number of individually controlled elements 116 mounted on a distal (outward) facing surface 118 (best seen in FIG. 2) of the transducer 102. Each transducer element 116 may itself comprise one or more (adjacent) piezoelectric members electrically connected to a same drive signal supplied from a system controller 106. During operation, the individual piezoelectric members each contribute a fractional part of the ultrasound energy beam 112 by converting the respective electronic drive signal into mechanical motion and resulting wave energy. The wave energy transmitted from the individual piezoelectric members of the transducer elements 116 collectively forms the acoustic energy beam 112, as the respective waves converge at the focal zone in the targeted tissue mass 104. Within the focal zone, the wave energy of the beam 112 is absorbed (i.e., attenuated) by the tissue, thereby generating heat and raising the temperature of the tissue to a point where the cells are denatured ("ablated").

An imager (e.g., an MRI system) 114 is used to generate three-dimensional images of the targeted tissue mass 104 before, during, and after the wave energy is delivered. The images are thermally sensitive so that the actual thermal dosing boundaries (i.e., the geometric boundaries and thermal gradients) of the ablated tissue may be monitored. The location, shape, and intensity of the focal zone of the acoustic beam 112 is determined, at least in part, by the physical arrangement of the transducer elements 116 and the physical positioning of the transducer 102. The location, shape, and intensity of the focal zone may also be controlled, at least in part, by controlling the respective output (e.g., phase and amplitude) of the individual transducer elements 116 by a process known as "electronic steering" of the beam 112. Examples of such physical positioning systems and techniques, and of electronic beam steering, including driving and controlling the output of individual transducer elements, can be found in U.S. Pat. Nos. 6,506,154, 6,506,171, 6,582,381, 6,613,004 and 6,618,620, which are all incorporated by reference herein.

In order to accommodate variations in treatment procedures and to access interior body regions that are difficult if not impossible to treat with a more conventional, e.g., spherical cap, ultrasound transducer, it may be desirable to employ an ultra-dense transducer array containing a relatively large number of individual elements. Although each element is preferably relatively small, such as on the order of the wavelength of the acoustic energy transmitted, given the large number of available elements, it would only be necessary to activate a relatively small subset of such elements in order to deliver a sufficient amount of acoustic energy to the focal zone. However, individual drive signals would still have to be provided to each transducer element in order for the transducer element to transmit energy, and it would still be desirable to be able to activate any given element with any one of a number of possible drive signal phases, in order for the transducer array to achieve an optimal performance. While a switching mechanism may be used to connect an appropriate drive signal to the respective transducer elements, as the number of transducer elements grows, a conventional switching mechanism would become cumbersome and cost-prohibitive to employ and control.

SUMMARY OF THE INVENTION

In accordance with one aspect of the invention, systems and methods are provided for selectively connecting respective drive signals to respective transducer elements of an ultra-high density array of transducer elements in a focused ultrasound system. In one implementation, an ultrasonic transducer used for transmitting acoustic energy for thermal tissue treatment includes a relatively large number of transducer elements. By way of non-limiting example, the transducer may take the form of a flexible or semi-flexible strip that may be attached directly or indirectly to an exterior body surface for delivering targeted acoustic energy to tissue in an internal region of the body. The individual transducer elements may be individually formed or provided on relatively small substrates (e.g., with each substrate comprising an array of transducer elements) that are attached to the transducer body. In order to drive the selected transducer elements at the appropriate phases, a drive signal generator may be employed to generate a number of possible drive signals having the same frequency, each drive signal being out of phase with the others by a selected phase offset amount. A two-tier hierarchical switching fabric is then employed to connect selected drive signals to selected transducer elements that are to be activated for a given tissue sonication.

In one embodiment, a first tier of the switching fabric selects a drive signal to be supplied to an identified subset of one or more transducer elements, and a second tier of the switching fabric connects the selected drive signal to the identified transducer element(s). In one embodiment, the first tier is implemented as a plurality of first tier switching modules, and the second tier is implemented as a plurality of second tier switching modules. Each first tier module has a number of inputs, each input coupled to a respective drive signal, where the number of inputs is equal to the number of drive signals. The inputs are selectively connectable to a common first tier module output via a respective first tier switch, e.g., a transistor or MEMs device. A respective drive signal selection control signal is received by the first tier modules for causing a selected one of the first tier switches to be activated to thereby couple a selected one of the drive signals to the respective first tier module output.

Each second tier switching module has a common input that is connected to an output of a respective first tier module. The second tier module inputs are selectively connectable to one or more second tier module outputs via a plurality of respective second tier switches, e.g., transistors and/or MEMs devices. Respective element selection control signals are received by the second tier modules for causing selected ones of the second tier switches to be activated, thereby coupling the respective drive signals to the selected second tier outputs. Individual groups of k transducer elements are connected (e.g., hard-wired or by using individual summing networks) to respective outputs of the second tier modules, where the n total transducer elements are connected in groups of k elements each to n/k total second tier modules.

The respective first and second tier switching modules may be provided in a substantially 1:1 ratio, where the output of a given first tier switching module is directly connected to the input of a second tier switching module. It will be appreciated that the physical implantation of the two-tier switching fabric need not necessary take for form of distinct first and second "modules," and that embodiments of the invention make take a variety of physical forms.

Other and further aspects and features of embodiments of the invention will become apparent in view of the following detailed description and illustrated embodiments.

BRIEF DESCRIPTION OF THE DRAWINGS

The invention is illustrated by w ay of example and not limitation in the figures of the accompanying drawings, in which like references indicate similar elements, and in which.

DETAILED DESCRIPTION

In the following description, references to "one embodiment" or "an embodiment" mean that the feature being referred to is included in at least one embodiment of the invention. Further, separate references to "one embodiment" in this description do not necessarily refer to the same embodiment; however, neither are such embodiments mutually exclusive, unless so stated and except as will be readily apparent to those skilled in the art. In particular, the invention can include any variety of combinations and/or integrations of the embodiments described herein.

The invention relates to systems and methods for selectively coupling one of a number of discrete drive signals to selected transducer elements of a high density array. The transducer elements of the array may be divided into individual groupings, with each grouping of transducer elements selectively coupled to a respective drive signal. In this manner, each transducer element in a given grouping may operate with the same phase. It may be desirable to connect only a single transducer element of a particular grouping to a respective drive signal, or it may be preferable to connect more than one transducer element of a grouping to a drive signal. In alternate embodiments (not depicted or further described herein), each grouping may be selectively coupled to multiple drive signals using a summing network, which is a network of passive components wired between adjacent transducer elements. This alternate approach enables manipulation and variation of the otherwise limited number of drive signals that are available to supply to the respective transducer element groupings. Briefly, the summing networks compose corrected drive signals from the planned drive signals and the relationship(s) between the adjacent elements. These networks are static and may represent a way to correct for geometric adjustments and any trimming of the drive signal, which may be pre-calculated and pre-adjusted by a static shift or summing the drive signals of adjacent transducer elements. In such alternate embodiments, each transducer element in a given grouping may operate with a phase that is a product of the particular summing network. Again, it may be desirable to connect only a single transducer element of a grouping to the respective phase signal, or it may be preferable to connect more than one transducer element to the signal.

More particularly, a switching network according to embodiments of the invention is designed to rout appropriate drive signals to each transducer element of the transducer array using minimum number of source signals in order to drive a very large community of transducer elements in the array. The switching network employs switching modules which enable dynamic routing of drive signals to any specific element by employing a hierarchical approach.

In one implementation, a multi-tier switching fabric is provided to connect one or more of each grouping of transducer elements with a selected drive signal. A first tier of the switching fabric receives a plurality of drive signals and selectively outputs a single drive signal with a particular phase offset. A second tier of the switching fabric receives and couples the selected drive signals to selected ones or groupings of the transducer elements. For example, the first tier of the switching element may select a first drive signal with a first phase offset for a first grouping of transducer elements, and a second drive signal with a second phase offset for a second grouping of transducer elements. The second tier switching fabric may include a number of second tier switching modules, such as, for example, one second tier switching module for each grouping of transducer elements. Each second tier switching module receives a respective drive signal output from the first tier switching fabric, and selectively couples the received drive signal to one or more transducer elements connected to that module that are to be activated for a given sonication.

Figure 3:
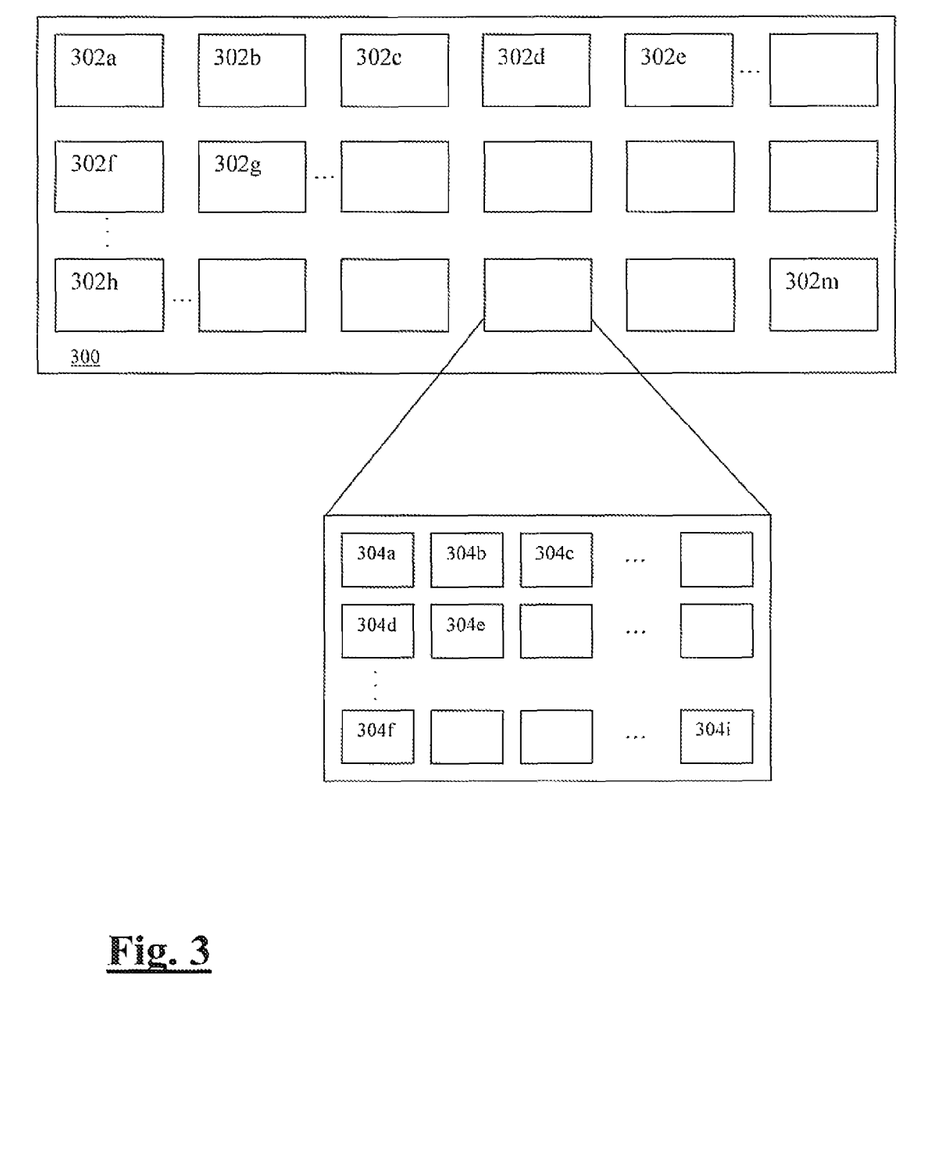
FIG. 3 is a simplified schematic illustration of an ultra-high density transducer element array.

As shown in FIG. 3 a transducer 300 constructed according to one embodiment includes a high density array of individual transducer elements 304 for generating acoustic wave energy in a focused ultrasound system. In various embodiments, the transducer 300 may be implemented, for example, as a flexible substrate or band that may be placed around and/or coupled to an exterior surface (skin) of a patient, e.g., in a belt-like fashion. In another embodiment, the transducer 300 may be alternatively be implemented as a rigid structure, which is directly or indirectly coupled to a patient. Other implementations of the transducer 300, including various geometries for implementing a flexible or rigid transducer will be apparent to those skilled in the art, and the invention is not to be limited by the particular transducer implementation. In the embodiment shown in FIG. 3, the transducer 300 comprises an array of transducer tiles, 302a-302m, with each tile 302 comprising an array of individual transducer elements 304a-304i. Thus, in embodiments in which each of the transducer tiles 302a-302m has a same (or substantially same) number of transducer elements 304i, the total number of transducer elements n is equal (or approximately equal) to m*i. The individual transducer elements 304a-304i of each tile are hard-wired to a switching front end (FIG. 4) in order to selectively couple activation drive signals to the elements for generating acoustic wave energy. For example, respective groupings of k transducer elements 304 may be hard-wired to corresponding outputs of respective switching modules (described below in conjunction with FIG. 4) associated with the switching front end.

The particular transducer elements that are connected to a given second tier module will be a design consideration and the connection patterns may vary among embodiments of the invention. For example, it may be desirable to select the locations of the k elements connected to a given second tier module based on achieving physical proximity or diversity of the respective individual elements in each grouping. Alternatively, it may be desirable to randomly connect the groupings of transducer elements to the respective switching modules, without any regard for the particular location on the transducer of the k elements. In one embodiment, the group size k corresponds to the number of transducer elements 304 located on a single tile 302, and the groupings are connected on a tile-by-tile basis. In another embodiment, the groupings comprise individual elements 304 located on different tiles 302. For example, each grouping may include one transducer element 304 from each tile 302a-302m, where the group size is m. In other embodiments, each grouping may include a differing number of transducer elements 304, which may be randomly or pseudo-randomly distributed across the respective tiles 302a-302n. Other implementations of the transducer element groups will be apparent to those skilled in the art. Moreover, the individual transducer elements 304 may be provided in different forms than on the tile arrays 302, which is just one example and embodiments of the invention may be useful and suitable for any transducer embodiment having a substantially high number of individually activatable elements, and are particularly suitable for ultra-high density arrays containing a relatively high number of individually activatable elements.

Although the individual transducer elements are preferably relatively small (and, thus, each transmits a relatively low power wave), what they lack in individual power output is made up for in the quantity of possible elements that may be simultaneously fired for a given sonication. Notably, a relatively small percentage of the total number of transducer elements (e.g., on the order of 5% or 10%) are typically activated for a given sonication. The individual transducer elements to be activated, along with the respective drive signal attributes (e.g., phase and amplitude) for each element, may be selected or determined by a planning system incorporated within the focused ultrasound system. The transducer elements may be "localized" relative to the local zone, e.g., by using a positioning systems to identify the respective locations of the transducer elements in a reference frame including the target tissue region and acoustic window (transmission path). This information, along with three-dimensional images of the internal body region including the target tissue region, can be used to identify a preferred and/or optimal combination of individual transducer elements to be activated. The element selection criteria may include many factors, such as, e.g., avoiding acoustic energy transmission through sensitive body tissue (e.g., ribs or lungs).

Figure 4A:
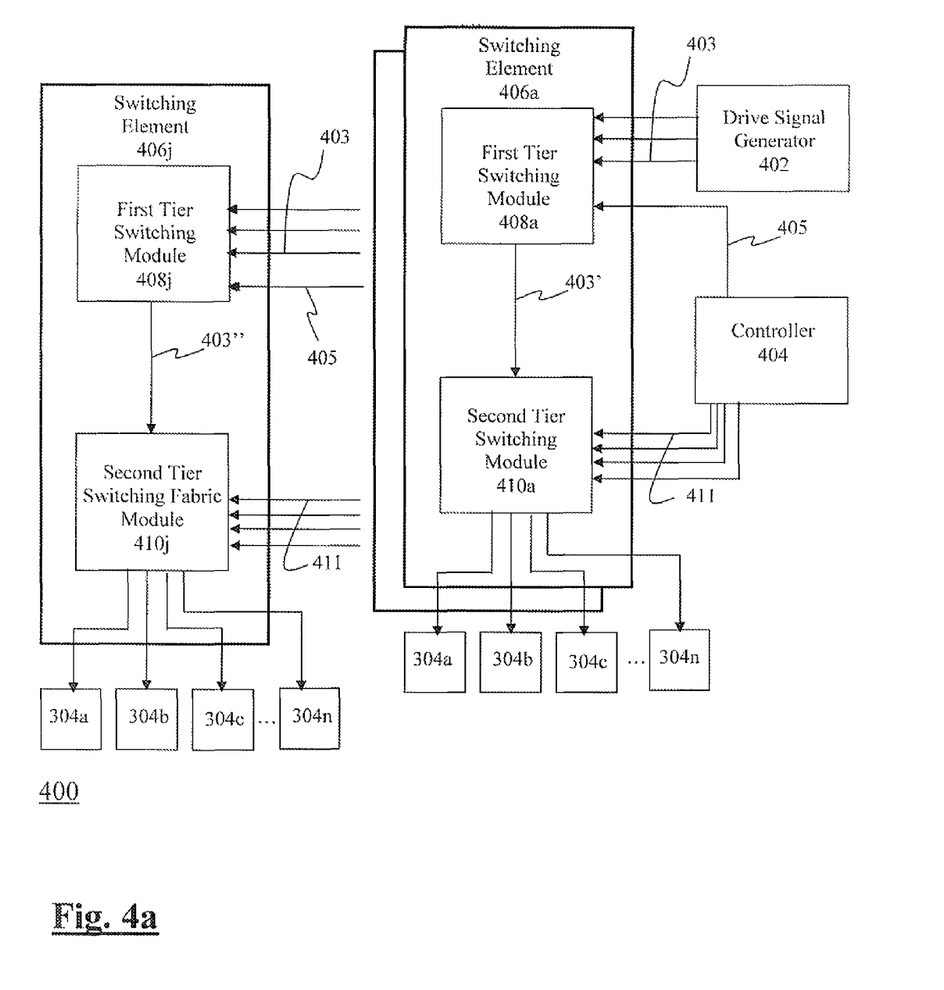
FIGS. 4*a-c* are simplified schematic illustrations of a control system including a multi-tier switching fabric for selectively connecting drive signals to individual transducer elements of an ultra-high density transducer array of a focused ultrasound system, in accordance with one embodiment of the invention.

FIG. 4a is a block diagram illustrating a first switching front end embodiment 400, which generally includes a drive signal generator 402, a controller 404, and a plurality of switching elements 406a-j. The drive signal (or "phasor") generator 402 generates a plurality of drive signals 403 at a selected frequency, that may be used to drive transducer elements 304a-304n, the use of transducer elements 304a-304n in all the switching elements 406a to 406j is for purposes of simplicity and is not intended to mean that the same elements are connected to all switching elements.

In particular, the respective drive signals 403 generated by the drive signal generator 402 are phase shifted from each other, such that each drive signal has a distinct phase offset from a base signal. By way of non-limiting example, in one embodiment, the drive signal generator 409 may supply twelve distinct drive signals 403 at a selected frequency, the drive signals being successively offset in phase by 30° each, i.e., where the respective drive signals are phase offset from a base signal (0°) by: 30°, 60°, 90°, 120°, 150°, 180°, 210°, 240°, 270°, 300°, and 330°.

Many other embodiments are also possible, e.g., the drive signal generator 402 may supply eighteen distinct drive signals 403 at a selected frequency and successively offset in phase by 20° each, i.e., 0°, 20°, 40°, 60°, 80°, 100°, 120°, 140°, 160°, 180°, 200°, 220°, 240°, 260°, 280°, 300°, 320°, and 340°. Other phases may also be combined to drive elements in embodiments that are driven from a summation network instead of from a single drive signal. It will be appreciated by those skilled in the art that it may be desirable to adjust the output power (amplitude) of the respective drive signals upward or downward, depending on the actual number of transducer elements the respective signals will drive during a given sonication, in order to reduce variations in the acoustic impedance of the individual acoustic waves as they converge in the focal region.

The controller 404 outputs control signals that are used to control switching elements 406a-j. Each of the switching elements 406a-j operates to select one drive signal 403' from the plurality of drive signals 403 generated by the drive signal generator 402, and to provide the selected drive signal 403' to selected ones of the transducer elements 304a-304n, as specified by the controller 404.

In one implementation, each of the switching elements 406a-j is a hierarchical switching element that includes, for example, a first tier switching module 408a-j, and a second tier switching module 410a-j. The first tier switching module 408a-j may be used to select one drive signal 403' from the plurality of drive signals 403 output by the drive signal generator 402, and the second tier switching module 410a-j may be used to provide the selected drive signal 403' to selected ones of the switching elements 304a-304n.

Figure 4B:
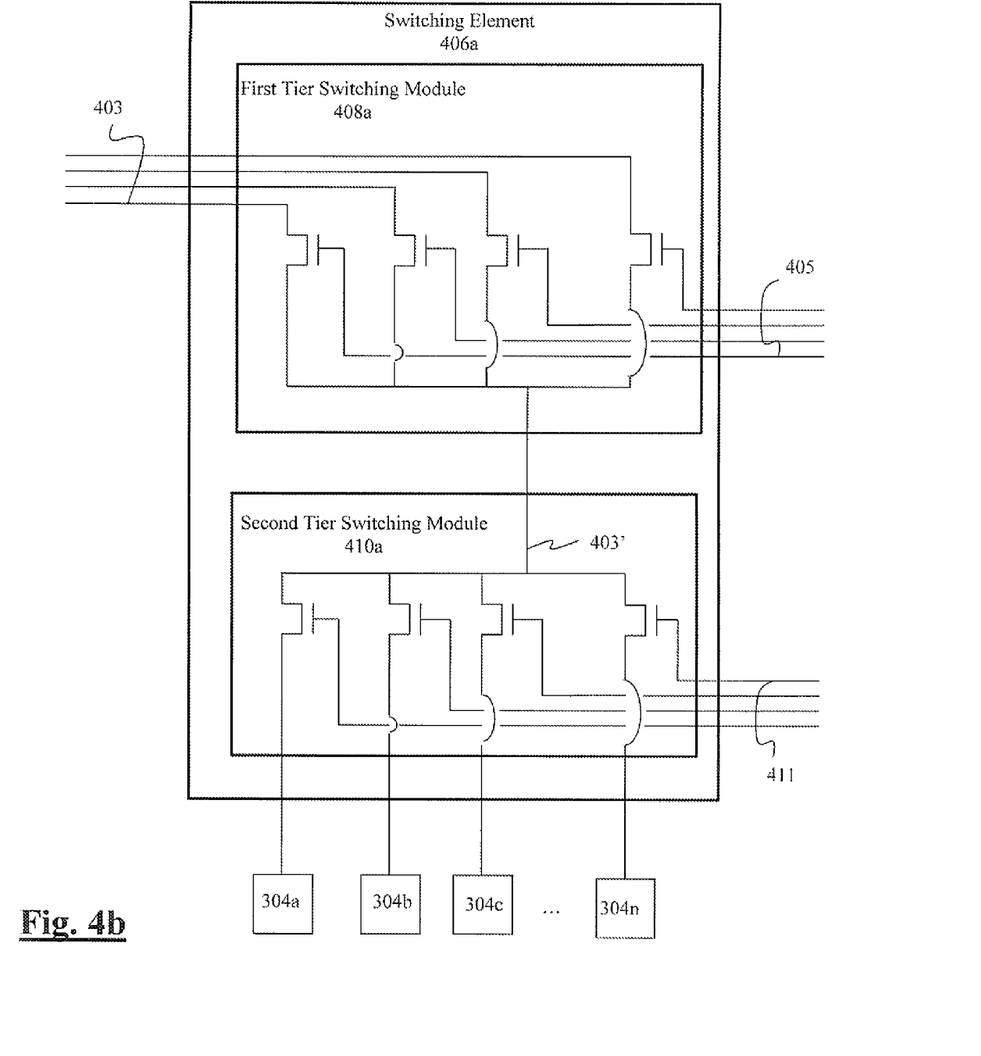

As shown in FIGS. 4a and 4b, the first tier switching module 408a receives a plurality of drive signals 403 from the drive signal generator 402, and receives a drive signal selector 405 from the controller 404. The first tier switching module 408a operates to select one drive signal 403' from the plurality of drive signals 403 based on the drive signal selector 405, and outputs the selected drive signal 403' to the second tier switching module 410.

The drive signal selector 405 contains sufficient information to allow the first tier switching module 408a to select one drive signal 403' from the plurality of drive signals 403. The drive signal selector 405 may contain a plurality of signals, as shown in FIG. 4b, or may contain a single signal, as shown in FIG. 4a. In one implementation, the first tier switching module 408a may contain a de-multiplexer that allows a single drive signal selector 405 to be used.

Figure 2:
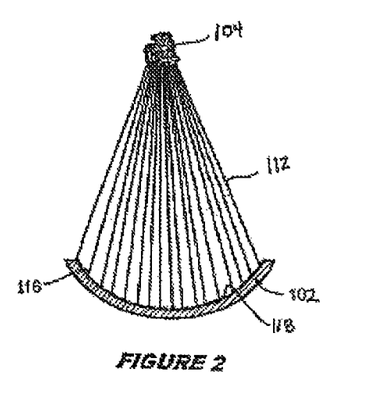

As shown in FIGS. 4a and 4b, the second tier switching module 410 receives a selected drive signal 403' from the first tier switching module 408a, and receives one or more transducer element selectors 411 from the controller 404. The information received in the one or more transducer element selectors 411 may be sufficient to describe which of the transducer elements 304a-n in the grouping are to be turned on at a particular time. Although the one or more transducer element select signals 411 are depicted in FIG. 2 as a plurality of signals received in parallel, those skilled in the art will appreciate that the one or more transducer element select signals 411 could be received in series or in parallel. Furthermore, those skilled in the art will appreciate that the one transducer element select signal 411 could be provided to the second tier switching module 410a, that a number of transducer element select signals 411 equal to the number of transducer elements 304a-n in the grouping could be provided to the second tier switching module 410a, or that another number of transducer element select signals 411 could be provided. In one implementation, the second tier switching module 410a contains a de-multiplexer that allows a single input signal 411 to be used.

The information received in the one or more transducer element selectors may be sufficient to describe which of the transducer elements 304a-304n in the grouping are to be turned on at a particular time. Based on the one or more transducer element selectors, the drive signal received from the first tier switching module 408a-b is provided selectively to those transducer elements that are to be turned on.

While the switching mechanism has been described in terms of discrete switching elements 406a-j, each switching element including a first tier switching module 408a-j and a second tier switching module 410a-j, other implementations of the switching mechanism will occur to those skilled in the art. In particular it is contemplated that a single first tier switching module 408 may be provided for a plurality of second tier switching modules 410a-j. Other configurations will occur to those skilled in the art. Alternate configurations for the switching fabric are illustrated in FIG. 4c.

Figure 4C:
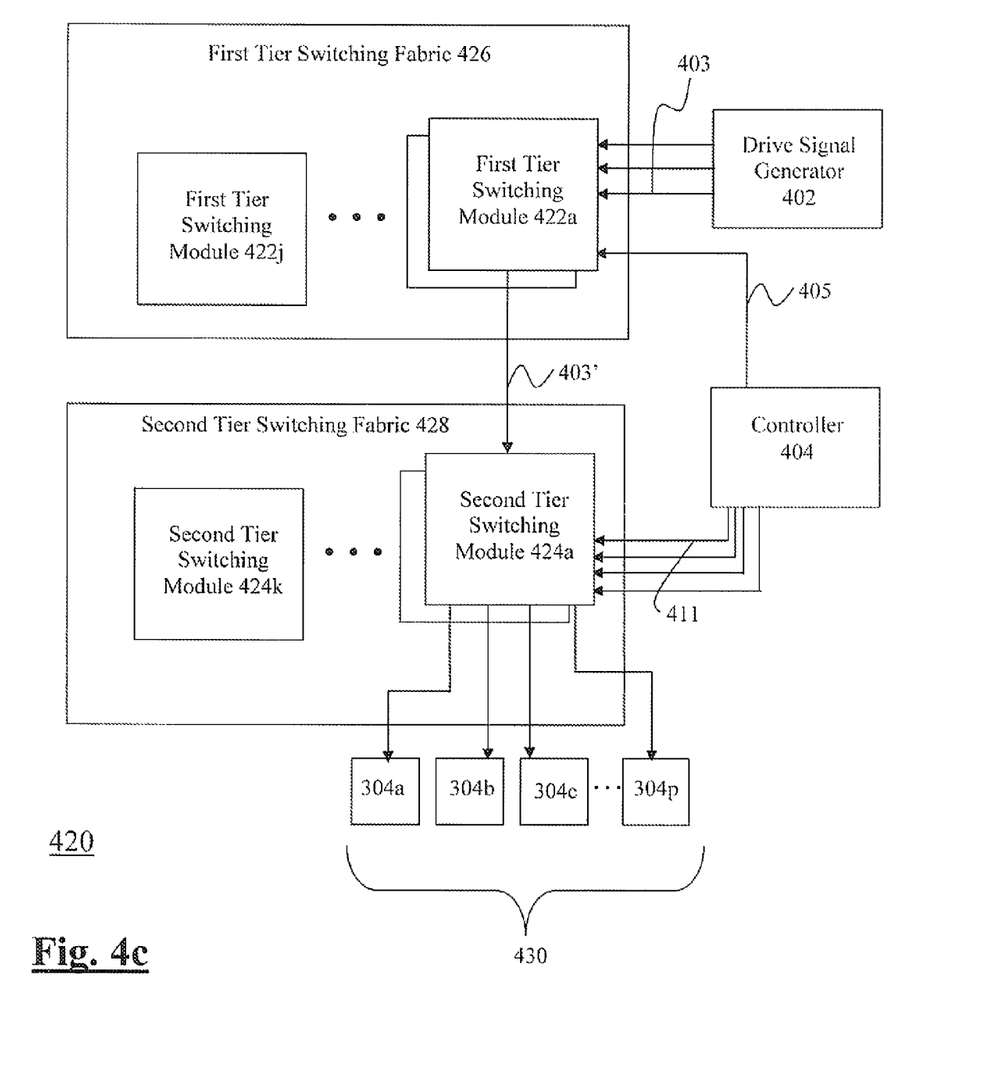

FIG. 4c is a block diagram illustrating a system for switching transducer elements ("switching front end"). The system 420 of FIG. 4c is similar to the system 400 of FIG. 4a. However, in the system 420 of FIG. 4c, the mapping of first tier switching modules to second tier switching modules need not be one to one. In particular, the system 420 of FIG. 4c may include a single first tier switching module 422a that provides drive signals to a plurality of second tier switching modules 424a-k.

As shown in FIG. 4c, the system 420 may include a drive signal generator 402 and a controller 404, similar to those discussed above with reference to FIG. 4a. Furthermore, the system 420 may include a first tier switching fabric 426 and a second tier switching fabric 428. The first tier switching fabric 426 may be made up of one or more first tier switching modules 422a-j, and the second tier switching fabric 428 may be made up of one or more second tier switching modules 424a-k.

Each of the first tier switching modules 422a-j may be coupled to one or more second tier switching modules 424a-k. Each of the first tier switching modules 422a-j may be configured to output one drive signal 403' to each of the second tier switching modules 424a-k coupled to it. The first tier switching modules 422a-j need not output the same drive signal to each of the second tier switching modules 424a-k, but may provide a first drive signal 403' to a second tier switching module 424a, a second drive signal 403" to another second tier switching module 424b, and so on.

Each of the second tier switching modules 424a-k may be associated with one grouping 430 of transducer elements 304a-p. Each of the second tier switching modules 424a-k may be coupled to the transducer elements 304a-p in the grouping 430. Each of the second tier switching modules 424a-k may receive one drive signal 403' from a first tier switching module 422a-j, and may output the received drive signal 403' to selected ones of the transducer elements 304a-p in the grouping 430.

As discussed above with reference to FIG. 3, each grouping 430 of transducer elements 304a-p may include, for example, a plurality of transducer elements that may be located on one tile, or may include a plurality of transducer elements located, for example, on a plurality of tiles. In alternate embodiments, the transducer elements may not be located on tiles but may nevertheless be formed into groupings.

In one implementation, each of the first tier switching elements 422a-j receives a plurality of drive signals 403 from the drive signal generator 402, and receives one or more drive signal selectors 405 from the controller 404. The first tier switching elements 426a-j operate to select a drive signal 403' from the plurality of drive signals 403 for each of the second tier switching elements 424a-k coupled to it, based on the drive signal selectors 405. Each of the first tier switching elements 422a-j outputs the appropriate selected drive signal(s) 403' to each of the second tier switching modules 494a-k coupled to it.

Each of the second tier switching modules 424a-k receives a selected drive signal 403' from a first tier switching module 422a-j, and receives one or more transducer element selectors 411 from the controller 404. The information received in the transducer element selectors 411 may be sufficient to describe which of the transducer elements 304a-p in the grouping 430 are to be turned on at a particular time. Based on the transducer element selectors 411, the drive signal 403' received from the first tier switching module 422a-j is provided selectively to those transducer elements 304a-p that are to be turned on.

While the switching mechanism has been described in terms of discrete first tier switching modules 422a-j coupled to second tier switching modules 424a-1k, other implementations will occur to those skilled in the art. In particular, it is contemplated that a single first tier switching module 422a may be provided for a plurality of second tier switching modules 424a-k. The single first tier switching fabric 422a may receive a plurality of drive signals 403 from the drive signal generator 402, and may output one drive signal 403' to each of the second tier switching modules 424a-k.

In another implementation, a number of first tier switching modules 422a-j may each be coupled to a number of second tier switching modules 424a-k. In this implementation, the number of second tier switching modules 422a-k coupled to each first tier switching module 424a-j may be limited, for example, to ensure that the signal strength is sufficient to drive the transducer elements 304a-p. Other implementations of the switching mechanism will occur to those skilled in the art.

In some implementations, each drive signal 403 may be applied to a varying number of transducer elements 304a-p, as each drive signal 403 may be provided to a varying number of second tier switching modules 424a-j, and as each of the second tier switching modules 424a-j may provide the drive signal 403 to varying numbers of transducer elements 305a-p. However, when the number of second tier switching modules 424 and the number of transducer elements 304a-p is large, statistical distribution may limit this variation. Thus, it may not be necessary to adjust the power of the drive signals 403 based on the load. However, in some implementations, the power of each drive signals 403 may be adjusted based on the number of transducer elements 304a-p to be driven. For example, the controller 404 may adjust the power of the drive signals 403.

Figure 5:
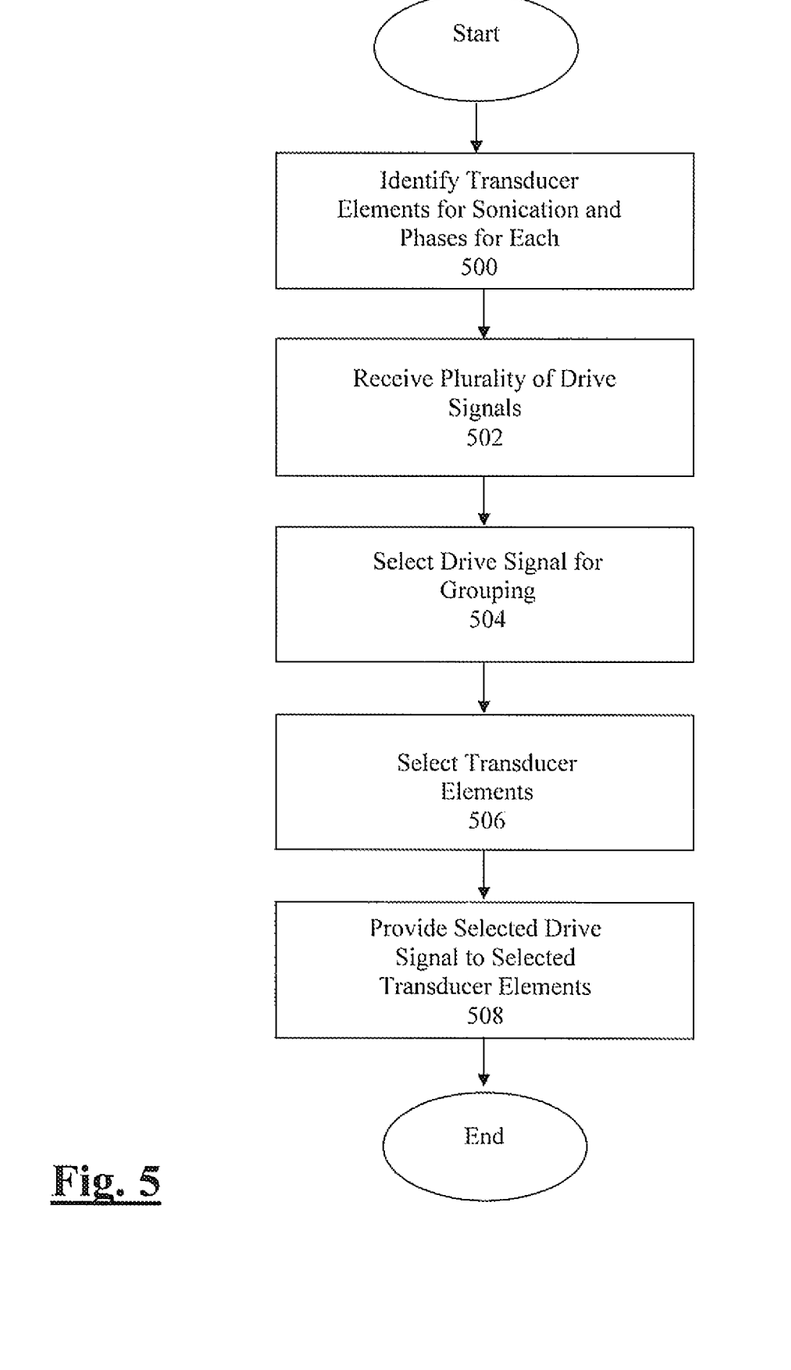
FIG. 5 is a flow chart illustrating a method for providing a selected drive signal to a plurality of selected transducer elements, in accordance with one embodiment of the invention.

FIG. 5 is a flow chart illustrating a method for providing a drive signal to a plurality of transducer elements. As shown in FIG. 5, the method may begin in step 500, wherein transducer elements may be identified for a given sonication, and, phases may be identified for each transducer element. Step 500 may be performed, for example, by a controller that receives image data, such as MRI data, and determines which transducer elements are to be turned on, and at which phase to operate each transducer element.

The method may continue in step 502, wherein a plurality of drive signals may be received. The plurality of drive signals may be received, for example, from a drive signal generator. The plurality of drive signals may be phase shifted such that each drive signal has a distinct phase.

The method may continue in step 504, wherein one drive signal may be selected from the plurality of drive signals. The drive signal may be selected, for example, based on a drive signal selector received from a controller.

In step 506, one or more transducer elements may be selected. The transducer elements may be selected, for example, from the grouping of transducer elements. The transducer elements may be selected based on one or more transducer element selectors that are received, for example, from a controller.

In step 508, the selected drive signal may be applied to the selected transducer elements. The drive signal may be applied, for example, to activate the transducer elements to produce ultrasound energy.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions shown in the process flow diagrams described herein is merely illustrative, and the invention can be performed using different or additional process actions, or a different combination or ordering of process actions.

For example, while the invention has been described in terms of one drive signal generator that outputs drive signals for all the transducer elements, it is contemplated that more than one drive signal generator may he provided. Each drive signal generator may be dedicated to provide a plurality of drive signals to specific switching mechanisms or to specific transducer elements. Alternatively or in addition, each drive signal generator may be dedicated to provide one or more signals with one or more particular phases. Further, as briefly described above, each grouping may be selectively coupled to multiple drive signals using a summing network to enable further manipulation of the available drive signals. In such alternate embodiments, each transducer element in a given grouping may operate with a phase that is a product of the particular summing network.

Accordingly, the specification and drawings are to be regarded in an illustrative, rather than restrictive sense.

What is claimed is:

1. A method of delivering target acoustic energy to body tissue using a transducer having a plurality of transducer elements, the method comprising:
   identifying a subset of transducer elements to be activated in order to transmit a targeted acoustic energy burst from the transducer;
   simultaneously providing as inputs to each of a plurality of first tier switching modules a plurality of drive signals having different phases;
   selectively outputting a respective one of the drive signals from each of the plurality of first tier switching modules based on a respective drive-signal selection signal received from a controller;
   providing as inputs to each of a plurality of second tier switching modules a respective one of the drive signals output from the first tier modules, each second tier module being fixedly connected to one of a plurality of groupings of transducer elements, and each of the plurality of transducer elements being part of one of the groupings; and
   for each of the plurality of second tier switching modules, selectively and simultaneously coupling the respective input drive signal, based on a respective transducer element selection signal received from the controller, to the identified transducer elements of the respective grouping, thereby activating the subset of transducer elements,
   wherein the subset of activated transducer elements consists of fewer than all of the transducer elements of at least one of the groupings.

2. The method of claim 1, wherein the transducer elements are implemented as a plurality of transducer element arrays, each array being formed on a separate substrate.

3. The method of claim 2, wherein substantially all of the transducer elements of at least one of the plurality of groupings are located on a single one of the arrays.

4. The method of claim 2, wherein substantially all of the transducer elements of at least one of the plurality of groupings are located on different arrays.

5. The method of claim 1, wherein at least some of the drive signals are supplied to first tier switching modules using respective summing networks.

6. A system for delivery of targeted acoustic energy to tissue, comprising:
   a transducer having a plurality of transducer elements;
   a controller;
   a plurality of first tier switching modules, the first tier modules simultaneously each receiving as inputs a plurality of drive signals having different respective phases, and configured to selectively output one of the drive signals based on a respective drive signal selection signal received from the controller; and
   a plurality of second tier switching modules fixedly connected to respective groupings of transducer elements, each of the plurality of transducer elements being part of one of the groupings, each second tier module receiving as an input a selected drive signal output from a respective first tier module, and being configured to selectively and simultaneously couple the drive signal, based on a respective transducer element selection signal received from the controller, to a plurality of transducer elements of the respective grouping of transducer elements, wherein the controller is configured to supply the respective drive signal selection signal and transducer element selection signals to the first and second tier switching modules in order to activate a selected subset of the transducer elements to thereby transmit a targeted acoustic energy burst, wherein the subset of activated transducer elements consists of fewer than all of the transducer elements of at least one of the groupings.

7. The system of claim 6, wherein the plurality of transducer elements are implemented as a plurality of transducer element arrays, each array being formed on a separate substrate.

8. The system of claim 7, wherein substantially all of the transducer elements of at least one of the groupings are located on a single one of the arrays.

9. The system of claim 7, wherein substantially all of the transducer elements of at least one of the groupings are located on different arrays.

10. The system of claim 6, further comprising a plurality of switching elements, each switching element comprising a respective first tier module and a respective second tier module, wherein the second tier module receives as an input the selected drive signal output from the first tier module of the same switching element.

11. The system of claim 6, further comprising a first tier switching fabric and a second tier switching fabric, the first tier fabric comprising the plurality of first tier modules and the second tier fabric comprising the plurality of second tier modules.

12. The system of claim 6, wherein at least some of the drive signals are supplied to first tier switching modules using respective summing networks.

* * * * *